United States Patent
Schmidt et al.

(10) Patent No.: US 6,264,660 B1
(45) Date of Patent: Jul. 24, 2001

(54) SURGICAL INSTRUMENT FOR MECHANICAL REMOVAL OF BONE CEMENT, AND PROCESS FOR PRODUCTION OF SHOCK WAVES

(75) Inventors: Joachim Schmidt, Gladbach; Wolfgang Merkle, Linnich; Andreas Menne, Meersburg, all of (DE); Bernard Simon, La Cure (FR); Denis Klopfenstein, Morges (CH)

(73) Assignee: Ferton Holding (CH)

( * ) Notice: Subject to any disclaimer, the term of this patent is extended or adjusted under 35 U.S.C. 154(b) by 0 days.

(21) Appl. No.: 09/202,136

(22) PCT Filed: Jun. 17, 1997

(86) PCT No.: PCT/EP97/03143

§ 371 Date: Dec. 9, 1998

§ 102(e) Date: Dec. 9, 1998

(87) PCT Pub. No.: WO97/48353

PCT Pub. Date: Dec. 24, 1997

(30) Foreign Application Priority Data

Jun. 19, 1996 (DE) ............................... 196 24 446

(51) Int. Cl.[7] .................................................. A61B 17/56
(52) U.S. Cl. ............................................. 606/100; 606/53
(58) Field of Search .............................. 600/104; 606/53, 606/79, 82, 86, 99, 100

(56) References Cited

U.S. PATENT DOCUMENTS

| | | | | |
|---|---|---|---|---|
| 2,376,187 | * | 5/1945 | Reiter | 433/151 |
| 2,421,354 | * | 5/1947 | Reiter | 606/100 |
| 2,437,014 | * | 3/1948 | Arnesen et al. | 606/100 |
| 2,655,921 | * | 10/1953 | Haboush | 606/84 |
| 2,725,878 | * | 12/1955 | Reiter | 606/79 |
| 3,640,280 | * | 2/1972 | Slanker et al. | 606/84 |
| 4,919,113 | * | 4/1990 | Sakamoto et al. | 128/4 |
| 5,518,502 | * | 5/1996 | Kaplan et al. | 600/157 |
| 5,902,413 | * | 5/1999 | Puszko et al. | 134/21 |
| 5,931,833 | * | 8/1999 | Silverstein | 606/1 |
| 5,980,528 | * | 11/1999 | Salys | 606/99 |

* cited by examiner

Primary Examiner—Paul J. Hirsch
Assistant Examiner—Michael B. Priddy
(74) Attorney, Agent, or Firm—Diller, Ramik & Wight.

(57) ABSTRACT

In a surgical instrument for the mechanical removal of bone cement (2), comprising a longitudinal housing (4) with a cylinder (6) in which a piston element can be reciprocated by a drive means (14), wherein the piston element on the distal end (18) of the cylinder (6) exerts an impact on a chisel tool supported axially in the housing (4), it is provided that the piston element (10) comprises a projectile (10) adapted to be accelerated to a high final speed and inducing a shock wave into the chisel tool comprising a metallic shock wave transmission probe (22), the probe tip (26) of the chisel tool transmitting the shock wave to the bone cement (2) at a low movement amplitude of the probe tip (26).

23 Claims, 3 Drawing Sheets

SURGICAL INSTRUMENT FOR MECHANICAL REMOVAL OF BONE CEMENT, AND PROCESS FOR PRODUCTION OF SHOCK WAVES

BACKGROUND OF THE INVENTION

The invention relates to a surgical instrument for the mechanical removal of bone cement according to the preamble of claim 1, and a process for the production of shock waves adapted for the removal of bone cement according to the preamble of claim 16.

Surgical instruments of the above type are required in orthopedic operations, for instance when after the removal of a hip joint prosthesis the remaining bone cement, e.g. made from PMMA, has to be removed, and for providing an accurate lodgment of the newly inserted hip joint prosthesis. For removing the cement, use is made e.g. of chisel tools which are driven into the cement with the aid of a hammer to thus split off the cement from the bone in the bone-marrow cavity.

The removal of bone cement is largely required in orthopedic surgery in order to exchange or consolidate date endoprostheses which have become loose or infected. Also other applications are possible.

Particularly in hip endoprosthetics, prostheses are exchanged with increasing frequency. In prostheses fixed by cement, the removal of the bone cement is bothersome and time-consuming. As of yet, the removal of the cement is performed by chisels of various shapes; however, such chisels pose problems as to their safe use, e.g. in the depth of the marrow cavity where visual inspection is difficult. Besides the large time requirements, damage may be caused to the bones, rendering the new implantation of a prosthesis impossible or resulting in an excessive loss of bone substance.

Further, pneumatic hammers are known (EP 0 144 005, WO95/22934) wherein a piston element is pneumatically reciprocated in a cylinder, wherein, at the distal end of the cylinder, the piston element exerts an impact onto a chisel tool axially supported in the housing. In such a system, the chisel tool is accelerated to speeds slightly above 3 m/s, and the stroke of the chisel tool is about 8 mm. The large stroke entails the danger that the chisel tool accidentally penetrates into the bone substance.

Thus, the above surgical instrument is merely suited to imitate the heretofore manually performed blow of a hammer. However, it has been found that the efficiency of such a pneumatically operated chisel does not meet the requirements in the removal of bone cement and involves the risk of damage to the bone.

Further known surgical instruments are operable to melt and remove thermoplastic bone cement by means of ultrasonic vibrations (U.S. Pat. No. 5,221,282). Using such an instrument, the bone cement will become ductile from about 100° C. and then can be removed. In the process, temperatures up to 200° C. are generated at the tip of the tool and may cause damage to the bone. The smoke generated during the removal of bone cement produces released monomers having a toxic effect.

SUMMARY OF THE INVENTION

Thus, it is an object of the invention to provide a surgical instrument for the removal of bone cement of the above mentioned type, and a process for the production of shock waves which is suited to remove bone cement with considerably increased effectiveness.

In the invention, it is advantageously provided that the piston element comprises a projectile which can be accelerated to a high final speed and induces a shock wave into the chisel tool comprising a shock wave transmission probe and having a probe tip transmitting the shock wave to the bone cement.

With the above ballistic gain, an undesired generation of heat is not to be expected, and the removal of cement is easily controllable. The time required for removing the cement, particularly when exchanging a prosthesis, is noticeably reduced. Cement can be removed without any substantial damage to the bone.

Thus, the transmission of the shock waves is not performed by a stroke of the whole chisel tool but substantially by the change of length of the shock wave transmission probe at the probe tip as induced by the shock wave. This makes it possible to generate high accelerations and speeds at the probe tip, allowing for the transmission of impact energy many times higher than in conventional pneumatically operated chisels because, in the laws of impact energy transmission, the speeds are reflected as raised to the second power.

The final speed of the projectile striking onto the shock wave transmission probe is about 5 to 20 m/s, preferably about 10 to 15 m/s. With such an impact velocity of the projectile, also an associated maximum speed of up to 20 m/s can be observed at the probe tip.

The velocity amplitude of the probe tip is below 1.5 mm and preferably less than 1 mm. The change of length is partially caused by the elastic deformation of the shock wave transmission probe and normally is between 0.5 and 1 mm on the whole.

The shock wave energy generated by the projectile is in the range between about 0.3 J and 2 J, preferably between about 0.5 J and 1.0 J.

The shock waves are generated by an impact frequency of the projectile of about 6 to 20 Hz, preferably about 8 to 10 Hz. The diameter of the shock wave transmission probe is in the range between about 1 and 6 mm, preferably between 2 and 4 mm.

The shock wave transmission probe is guided axially in the housing, and a damping spring element, acting in the axial direction, is arranged between the shock wave transmission probe and the housing. In this manner, the shock wave transmission probe is decoupled from the housing in the axial direction.

Further, it can be provided that the projectile transmits the impact pulse onto an intermediate element arranged in flush abutment on the shock wave transmission probe.

The shock wave transmission probe can be hollow, and the intermediate element can comprise a shell being closed towards its proximal end and having at least one radial outlet opening. Such an intermediate element in connection with a hollow shock wave transmission probe is suited for connection of a suction means for sectional removal of the detached bone cement.

The acceleration path of the projectile is preferably about 100 to 200 mm. Thus, the acceleration path is a multiple of the diameter of the projectile.

The shock wave transmission probe can be flexible so that the shock wave cannot be transmitted in a rectilinear fashion.

Further, a magnetic holder for the projectile can be arranged on the proximal end of the cylinder. The magnetic holder will hold the projectile in the proximal final position until the projectile is again accelerated towards the shock wave transmission probe.

Preferably, pneumatic drive means are provided to accelerate the projectile.

The shock wave transmission probe can be guided in a working channel of an endoscope. The optically monitored local use of the probe tip on the cement also in the depth region of the marrow cavity which otherwise cannot be visually observed, will increase the effectiveness of the cement removal as well as reduce the danger of undesired damage to bones and soft parts. This obviates the need for additional operative measures, e.g. the forming of bone windows.

Further, the endoscope can be provided with a lens cleansing means on the distal end. For cleansing, the optical lens of the endoscope is rinsed at the distal end of the. endoscope, preferably with $Co_2$.

An embodiment of the invention will be explained in greater detail hereunder with reference to the drawings.

DESCRIPTION OF THE PREFERRED EMBODIMENTS

Figure 1:
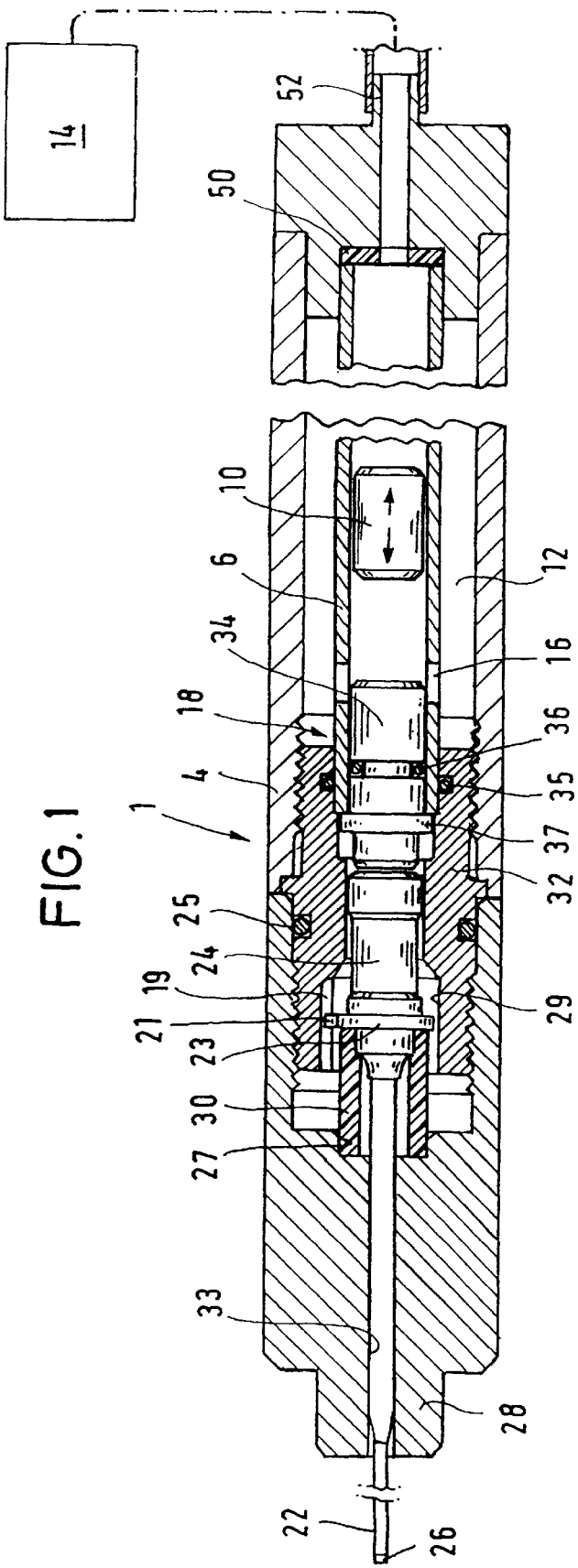
FIG. 1 shows a systematic cross-sectional view of the surgical instrument.

The hand-picked 1 illustrated in FIG. 1 comprises a housing 4 accommodating a pneumatic cylinder 6 wherein a projectile 10 is reciprocated between two end positions by pneumatic drive means 14 in combination with a pressure-head chamber 12 surrounding the cylinder 6 coaxially in the manner of a ring. By way of alternative, it is possible to accelerate the projectile 10 hydraulically, mechanically, electromagnetically or by explosive drive means. If the projectile 10 is accelerated electromagnetically, the acceleration path, which in case of a pneumatic drive has a length of about 100 to 200 mm, can be shortened.

In the proximal end position, the proximal end of cylinder 6 is provided with a magnet holder 52 which can hold the metallic projectile 10 in its proximal end position until the projectile 10 is again accelerated in the direction of the distal end 18 of cylinder 6 by a pneumatic pressure generated via connector hector (unnumbered). The air arranged ahead of the projectile 10 when seen in the moving direction of projectile 10 is guided into the pressure-head chamber 12 via at least one opening 16 formed at the distal end of cylinder 6. Due to its acceleration, the projectile 10 impinges with a high final speed of e.g. 15 m/s onto an intermediate member 34 arranged in the distal end 18 of cylinder 6 and allowing a shock transmission to a chisel tool arranged flush on the intermediate member 34. The chisel tool comprises a metallic shock wave transmission probe 22 transmitting the shock wave induced via the projectile 10 and the intermediate member 34 onto the bone cement 2 which is to be removed in a bone marrow cavity. The intermediate member 34 serves for hermetically sealing the housing 4 on the distal end 18 so that only the shock wave transmission probe 22 and a headpiece 28, to be screw-fitted onto housing 4, have to be sterilized.

Upon lapse of the pressure supplied to the pneumatic connector (unnumbered), the pressure head building up in the pressure-head chamber 12 is sufficient for moving the projectile 10 from the distal end position on the intermediate member 34 to the proximal end position at the magnet holder 50. The pneumatic pressure at connector (unnumbered) can be up to 5 bar. The projectile 10 can be selected differently for adaptation to specific lengths of the shock wave transmission probe 22 or for generating a specific characteristic of the shock wave with regard to its length, mass and maximum impact speed.

The impact energy transmitted to the shock wave transmission probe is about 0.3 to 2 J, while already a value of about 1 J leads to a high efficiency in the removing of bone cement.

Preferably, however, the metallic shock wave transmission probe 22 does not necessarily extend coaxially to cylinder 6 and projectile 10. The proximal end 24 of shock wave transmission probe 22 preferably has a diameter corresponding to the diameter of intermediate member 34 and the diameter of projectile 10. The length of projectile 10 is always larger than the diameter thereof. This allows for improved guiding characteristics within cylinder 6. Further, with the aid of a different length of the projectile 10, the mass of the projectile can be varied in a simple manner without the need to change the diameter of the intermediate member 34 or of the proximal end 24 of shock wave transmission probe 22. The ratio between the length and the diameter of projectile 10 is about 2.5:1 to 5:1.

The proximal end 24 of shock wave transmission probe 22 is axially supported in a guide opening 29 of a connecting element 32 which also accommodates the intermediate member 34 and the distal end 18 of cylinder 6 and can be screwed into housing 4 coaxially to cylinder 6. The intermediate member 34 is arranged for movement in the distal end 18 of cylinder 6 and sealed against cylinder 6 by an 0-ring 36. When the intermediate member 34 is subjected to an impact by projectile 10, the intermediate member can move forward in the distal direction in accordance with the deformation of the spring/damping element 30, while the intermediate member 34 under the influence of the restoring force of the spring/damping element 30 is compressed into its proximal end position where a collar 37 abuts the distal end face of cylinder 6. The connecting element 32 is sealed by an O-ring 35 against the outer surface of cylinder 6. For instance, by providing a flattened portion on the proximal end 24 or on a collar 23 at the proximal end 24, and a guide opening 29 in connecting element 32 adapted to this flattened portion, an anti-torsion protection can be created for the shock wave transmission probe 22. In FIG. 1, the collar 23 has a projection 21 arranged thereon which, acting as an anti-torsion protection means, engages a corresponding groove 19 of connecting element 32.

On the distal side of connecting element 32, headpiece 28 is screw-fitted flush with housing 4 and sealed by an O-ring 25 seated on connecting element 32. The connecting element 32 axially guides the shaft of shock wave transmission probe 22 in a bore 33 and accommodates a tubular spring/damping element 30 made e.g. from silicone. The spring/damping element 30 acts in the axial direction and decouples the shock wave transmission probe 22 in the axial direction from headpiece 28 and housing 4, respectively. For this purpose, the proximal end 24 of shock wave transmission probe 22 is provided with a collar 23 for abutment of the spring/damping element 30 thereon. The spring/damping element 30 is seated in a cylindrical recess 27 of headpiece 28. In the distal direction behind the collar 23, the diameter of the shock wave transmission probe 22 decreases to a shaft diameter of about 2 to 4 mm, e.g. 3.2 mm. The ratio between the projectile diameter and the shaft diameter is about 2:1 to 3:1. With such a ratio, the moving stroke at the probe tip 26 can be limited to a small amount.

The probe tip 26 is provided in the form of a chisel tool. The shock wave transmission probe 22 can also be formed as a hollow tool to allow a sectional removal of the detached bone cement 2.

In this case, also the intermediate member 34 can be provided as a shell being open in the distal direction and having a radial outlet opening adapted for attachment of a connector for sectional removal.

The shock waves are generated with an impact frequency between 6 and 20 Hz, while an impact frequency of 10 Hz is particularly useful for the removal of bone cement. The probe tip 26 performs a moving stroke of maximally about 1,5 mm and preferably less than 1 mm. A portion of this movement of probe tip 26, about 0.3 mm, is generated by an extension of the shock wave transmission probe 22 due to the shock wave, while the rest of the moving stroke is generated by a deformation of the spring/damping element 30. The portion generated by the shock wave accounts for about 30% of the complete moving stroke which reaches its maximum value after about 1 ms. The shock wave, which is reflected at the ends of the shock wave transmission probe 22, generates oscillations superposed on the moving stroke of probe tip 26 and having steep rising flanks which are steeper than the rising flanks of the moving stroke and thus will contribute to a considerable increase of the probe tip speed. In this manner, the impact energy transmitted to the bone cement 2 can be by a factor of about 30 to 50 higher than in conventional pneumatic chisels.

The ratio between the projectile mass and the probe mass is about 1:2 to 1:10, preferably about 1:4 to 1:6. Thus, the mass of the projectile 10 is smaller than the mass of the shock wave transmission probe 22.

The length of projectile 10 determines the length of the shock wave. The ratio between the projectile length and the probe length is about 1:10 to 1:30, preferably about 1:15. Thus, the length of the induced shock wave is small in relation to the length dimension of the probe.

The ratio between the diameter of the probe shaft and the length of the probe is in the range between about 1:50 and 1:200, preferably in the range between 1:200 and 1:150. As already mentioned, a diameter of the probe shaft of about 2 to 4 mm is preferred. A probe of this type can be introduced into the working channel of an endoscope and allows for the use of the chisel tool in endoscopic operations. When using the shock wave transmission probe 22 in connection with an endoscope, it is possible to work permanently or intermittently in a liquid medium. This offers the advantage that a lens cleansing can be omitted in some cases. In such a case, however, it is necessary to seal the open region of the bone-marrow cavity with a suitable elastic plug.

Figure 2:
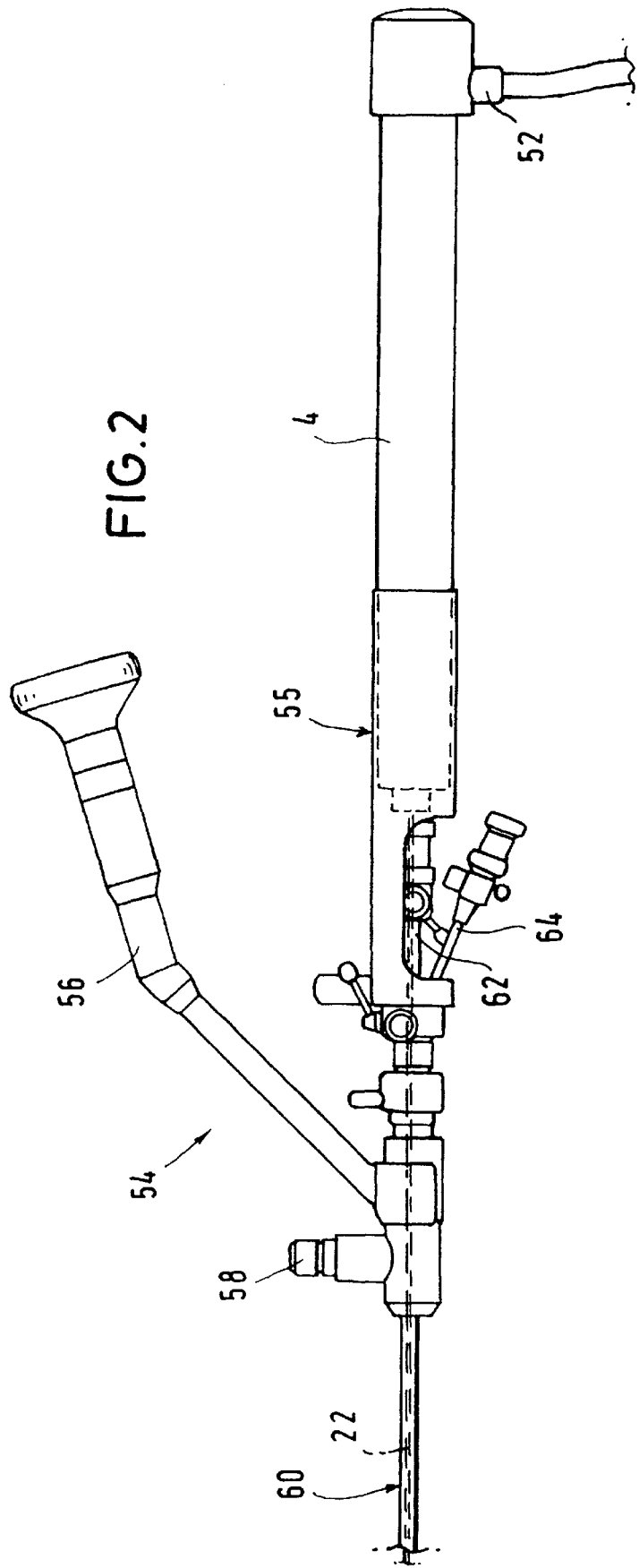
FIG. 2 shows the use of the surgical instrument in connection with an endoscope.
Figure 3:
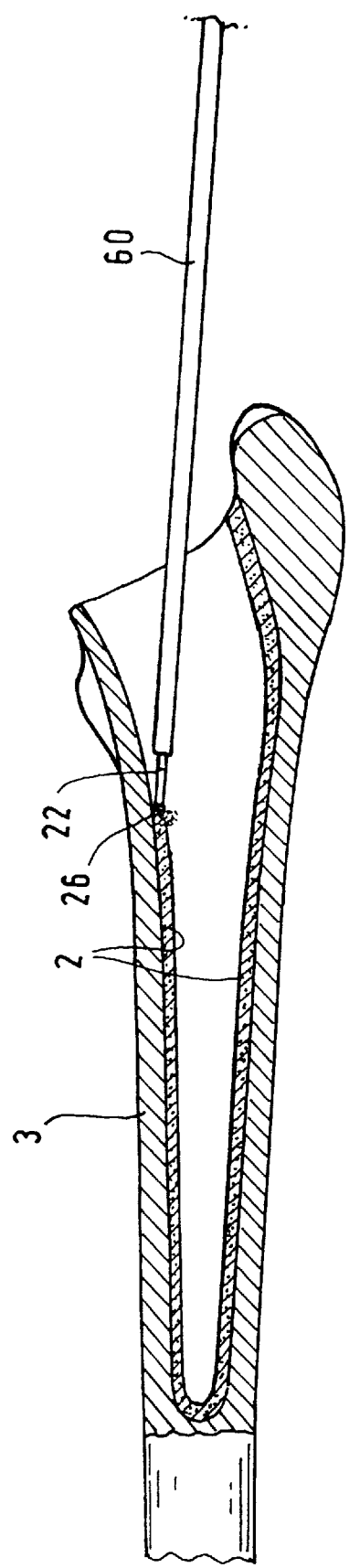
FIG. 3 shows the endoscope probe inserted into the bone-marrow cavity.

FIG. 2 illustrates the use of the surgical instrument in an endoscope. The shock wave transmission probe 22 is inserted in a first working channel 62 of the endoscope 54. By means of an ocular or eyepiece and through illumination by optical fibers via an optical fiber connector 58, the operating field of the chisel tool can be monitored. Using a second working channel 64 entering the endoscope probe 60 in a curved shape, liquids can be supplied or sucked, for instance. The coupling of housing 4 to endoscope 54 is performed by means of an adapter 55. The endoscope probe 60 allows for the removal of cement in regions in the depth of the marrow cavity which otherwise cannot be visually observed. By the endoscopic observation of the operation region, the danger of undesired damage to bones and soft parts is reduced. In case of an endoscopic use of the surgical instrument, additional operative measures, e.g. the forming of bone windows, are not required.

Although a preferred embodiment of the invention has been specifically illustrated and described herein, it is to be understood that minor variations may be made in the apparatus without departing from the spirit and scope of the invention, as defined the appended claims.

We claims:

1. A surgical instrument for the mechanical removal of bone cement comprising a longitudinal housing (4) housing a tubular cylinder (6) in which a piston projectile (10) can be reciprocated, means (14) for driving the piston projectile from a proximal end of the cylinder (6) toward a distal end (18) of the cylinder (6), a shock wave transmission probe (22) having a chisel tip (26) at its distal end and a proximal end (24) adapted to receive impact forces generated by said piston projectile (10), said shock wave transmission probe (22) being secured in a guide means (19,21) against torsion said driving means (14) being constructed and arranged for accelerating said piston projection (10) to a final speed of substantially 5 to 20 m/s thereby inducing a shock wave in the chisel tip (26) which is transmitted to the bone cement, means (30) for limiting the movement amplitude of the probe tip (26) to less than 1.5 mm, and said driving means (14) being constructed and arranged for transferring shock wave energy to said chisel tool (26) in the range of between substantially 0.3 J and 2 J.

2. The instrument according to claim 1, characterized in that the final speed of the piston projectile (10) is about 10 to 15 m/s.

3. The instrument according to claim 1, characterized in that the amplitude of the probe tip (26) is less than 1 mm.

4. The instrument according to claim 1, characterized in that the shock wave energy generated by the piston projectile (10) is in the range between about 0.5 J and about 1.0 J.

5. The instrument according to claim 1, characterized in that the impact frequency of the piston projectile (10) is about 6 to 20 Hz, preferably about 8 to 10 Hz.

6. The instrument according to claim 1, characterized in that the length of the probe is about 100 mm to 500 mm, preferably about 150 mm to 420 mm.

7. The instrument according to claim 1, characterized in that the diameter of the shock wave transmission probe (22) is in the range between about 1 and 6 mm, preferably between about 2 and 4 mm.

8. The instrument according to claim 1, characterized in that the shock wave transmission probe (22) is guided axially in the housing (4), and the means for limiting the movement amplitude of the probe tip (26) includes a damping spring element (30), acting in the axial direction, is arranged between the shock wave transmission probe (22) and the housing (4).

9. The instrument according to claim 1, characterized in that the piston projectile (10) transmits the impact pulse onto an intermediate element (34) arranged in flush abutment on the shock wave transmission probe (22).

10. The instrument according to claim 9, characterized in that the shock wave transmission probe (22) is hollow, and the tubular cylinder (6) has a radial opening (16) therein.

11. The instrument according to claim 1, characterized in that the acceleration path of the piston projectile (10) is preferably about 100 to 200 mm.

12. The instrument according to claim 1, characterized in that a magnetic holder (50) for the piston projectile (10) is arranged on a proximal end of the cylinder (6).

13. The instrument according to claim 1, characterized in that the shock wave transmission probe (22) is flexible.

14. The instrument according to claim 1, characterized in that the shock wave transmission probe (22) is guided in a working channel (61) of an endoscope.

15. The instrument according to claim 14, characterized in that the endoscope is provided with a lens cleansing means on a distal end.

16. The surgical instrument as defined in claim 1 including an intermediate member (34) disposed between said piston projectile (10) and said probe (22).

17. The surgical instrument as defined in claim 1 including an intermediate tubular connecting element (32) housed within said housing (4) and a headpiece (28) through which projects a distal end of said probe (22).

18. The surgical instrument as defined in claim 1 including an intermediate tubular connecting element (32) housed within said housing (4) and a headpiece (28) through which projects a distal end of said probe (22), an intermediate member (34) disposed between said piston projectile (10) and said probe (22), and said intermediate member (34) being housed at least in part in each of said intermediate connecting element (32) and housing (6).

19. The surgical instrument as defined in claim 1 including an intermediate tubular connecting element (32) housed within said housing (4) and a headpiece (28) through which projects a distal end of said probe (22), said cooperative means (19, 23) are carried one (23) by said probe (22) and one (19) by said tubular connecting element (32), an intermediate member (34) disposed between said piston projectile (10) and said probe (22), said intermediate member (34) being housed at least in part in each of said intermediate connecting element (32) and housing (6), and cooperative means including a collar (37) of said intermediate member (34) for limiting axial reciprocal movement thereof.

20. A surgical instrument for the mechanical removal of bone cement comprising a longitudinal housing (4) housing a tubular cylinder (6) in which a piston projectile (10) can be reciprocated, means (14) for driving the piston projectile from a proximal end of the cylinder (6) toward a distal end (18) of the cylinder (6), a shock wave transmission probe (22) having a chisel tip (26) at its distal end and a proximal end (24) adapted to receive impact forces generated by said piston projectile (10), said shock wave transmission probe (22) being secured by cooperative means (23,29) for substantially preventing rotation of said probe (22), said driving means (14) being constructed and arranged for accelerating said piston projection (10) to a final speed of substantially 5 to 20 ms thereby inducing a shock wave in the chisel tip (26) which is transmitted to the bone cement, means (30) for limiting the movement amplitude of the probe tip (26) to less than 1.5 mm, and said driving means (14) being constructed and arranged for transferring shock wave energy to said chisel tool (26) in the range of between substantially 0.3 J and 2 J.

21. The surgical instrument as defined in claim 20 including an intermediate tubular connecting element (32) housed within said housing (4) and a headpiece (28) through which projects a distal end of said probe (22), and said cooperative means (23,29) are carried one (23) by said probe (22) and one (29) by said tubular connecting element (32).

22. The surgical instrument as defined in claim 20 including an intermediate tubular connecting element (32) housed within said housing (4) and a headpiece (28) through which projects a distal end of said probe (22), said cooperative means (19, 23) are carried one (23) by said probe (22) and one (26) by said tubular connecting element (32), an intermediate member (34) disposed between said piston projectile (10) and said probe (22), and said intermediate member (34) being housed at least in part in each of said intermediate connecting element (32) and housing (6).

23. The surgical instrument as defined in claim 20, said cooperative means (22, 29) comprising a collar (23) having a flattened portion and a guide opening (29) configured to receive said flattened portion of said collar (23).

* * * * *